United States Patent
Vansickle et al.

(10) Patent No.: US 9,789,322 B2
(45) Date of Patent: *Oct. 17, 2017

(54) EXTERNAL DEVICE FOR DETERMINING AN OPTIMAL IMPLANTABLE MEDICAL DEVICE FOR A PATIENT USING INFORMATION DETERMINED DURING AN EXTERNAL TRIAL STIMULATION PHASE

(71) Applicant: Boston Scientific Neuromodulation Corporation, Valencia, CA (US)

(72) Inventors: Dennis A. Vansickle, Lancaster, CA (US); Robert D. Ozawa, Woodland Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,454

(22) Filed: May 2, 2016

(65) Prior Publication Data

US 2016/0243369 A1 Aug. 25, 2016

Related U.S. Application Data

(63) Continuation of application No. 14/271,176, filed on May 6, 2014, now Pat. No. 9,327,135.

(Continued)

(51) Int. Cl.
*A61N 1/378* (2006.01)
*A61N 1/372* (2006.01)
(Continued)

(52) U.S. Cl.
CPC ......... *A61N 1/378* (2013.01); *A61N 1/36014* (2013.01); *A61N 1/37235* (2013.01);
(Continued)

(58) Field of Classification Search
CPC .... A61N 1/3708; A61N 1/36017; A61N 1/37; A61N 1/372; A61N 1/3787;
(Continued)

(56) References Cited

U.S. PATENT DOCUMENTS 4,134,408 A 1/1979 Brownlee et al.
5,321,392 A 6/1994 Skakoon et al.
(Continued)

FOREIGN PATENT DOCUMENTS

CN 102500057 A 6/2012

OTHER PUBLICATIONS

"Boston Scientific Precision Spectra™ System Programming Manual," at 50 (Sep. 2012).
"International Standard ISO 14708-1," Clause 28.19 (2000).

*Primary Examiner* — Kennedy Schaetzle
(74) *Attorney, Agent, or Firm* — Lewis, Reese & Nesmith, PLLC (57) ABSTRACT

An external controller is disclosed for communicating with an external trial stimulator (ETS) for an implantable medical device. The external controller is programmed with a battery algorithm able to assist a clinician in choosing a suitable implant for the patient based on battery performance parameters estimated for a number of implants during an external trial stimulation phase that precedes implantation of the implant. The algorithm is particularly useful in assisting the clinician in choosing between a rechargeable-battery implant or a primary-battery implant for the patient.

21 Claims, 10 Drawing Sheets

Related U.S. Application Data (60) Provisional application No. 61/831,037, filed on Jun. 4, 2013.

(51) Int. Cl.
*A61N 1/36* (2006.01)
*A61N 1/08* (2006.01)

(52) U.S. Cl.
CPC ..... *A61N 1/37241* (2013.01); *A61N 1/37252* (2013.01); *A61N 1/08* (2013.01); *A61N 2001/37294* (2013.01)

(58) Field of Classification Search
CPC .............. A61N 1/3706; A61N 1/37241; A61N 2001/37294; A61N 1/36125; A61N 1/378; A61N 1/08
See application file for complete search history.

(56) References Cited

U.S. PATENT DOCUMENTS

| | | |
|---|---|---|
| 5,769,877 A | 6/1998 | Barreras |
| 6,070,103 A | 5/2000 | Ogden |
| 6,108,579 A | 8/2000 | Snell et al. |
| 6,516,227 B1 | 2/2003 | Meadows et al. |
| 6,760,625 B1 | 7/2004 | Kroll |
| 7,079,893 B2 | 7/2006 | Greatbatch et al. |
| 7,142,923 B2 | 11/2006 | North et al. |
| 7,274,168 B2 | 9/2007 | Tskukamoto et al. |
| 7,469,161 B1 | 12/2008 | Gandhi |
| 7,620,452 B1 | 11/2009 | Russie |
| 7,805,263 B2 | 9/2010 | Mack |
| 7,945,327 B2 | 5/2011 | Gandhi et al. |
| 8,131,365 B2 | 3/2012 | Zhang et al. |
| 8,214,164 B2 | 7/2012 | Gandhi et al. |
| 8,401,646 B2 | 3/2013 | Stadler et al. |
| 8,498,716 B2 | 7/2013 | Chen et al. |
| 8,577,474 B2 | 11/2013 | Rahman et al. |
| 8,676,310 B2 | 3/2014 | Burnes et al. |
| 8,812,128 B2 | 8/2014 | Kothandaraman |
| 9,327,135 B2 * | 5/2016 | Vansickle ............... A61N 1/378 |
| 2003/0078634 A1* | 4/2003 | Schulman ................ A61N 1/08 607/61 |
| 2003/0114899 A1 | 6/2003 | Woods et al. |
| 2005/0177198 A1 | 8/2005 | Norton et al. |
| 2005/0222631 A1 | 10/2005 | Dalal et al. |
| 2006/0195152 A1 | 8/2006 | Gerber et al. |
| 2007/0250126 A1 | 10/2007 | Maile et al. |
| 2010/0228324 A1 | 9/2010 | Lamont et al. |
| 2010/0305662 A1 | 12/2010 | Ozawa et al. |
| 2012/0101551 A1 | 4/2012 | Aghassian et al. |
| 2012/0123502 A1 | 5/2012 | Aghassian et al. |
| 2012/0277832 A1 | 11/2012 | Hussain |

\* cited by examiner

EXTERNAL DEVICE FOR DETERMINING AN OPTIMAL IMPLANTABLE MEDICAL DEVICE FOR A PATIENT USING INFORMATION DETERMINED DURING AN EXTERNAL TRIAL STIMULATION PHASE

CROSS-REFERENCE TO RELATED APPLICATIONS

This is a continuation of U.S. patent application Ser. No. 14/271,176, filed May 6, 2014, which is a non-provisional application of U.S. Provisional Patent Application Ser. No. 61/831,037, filed Jun. 4, 2013. Both of these applications are incorporated herein by reference in their entireties, and priority is claimed to both.

FIELD OF THE INVENTION

The present invention relates to implantable medical device systems, and in particular systems involving implantable stimulators.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

Figure 1:
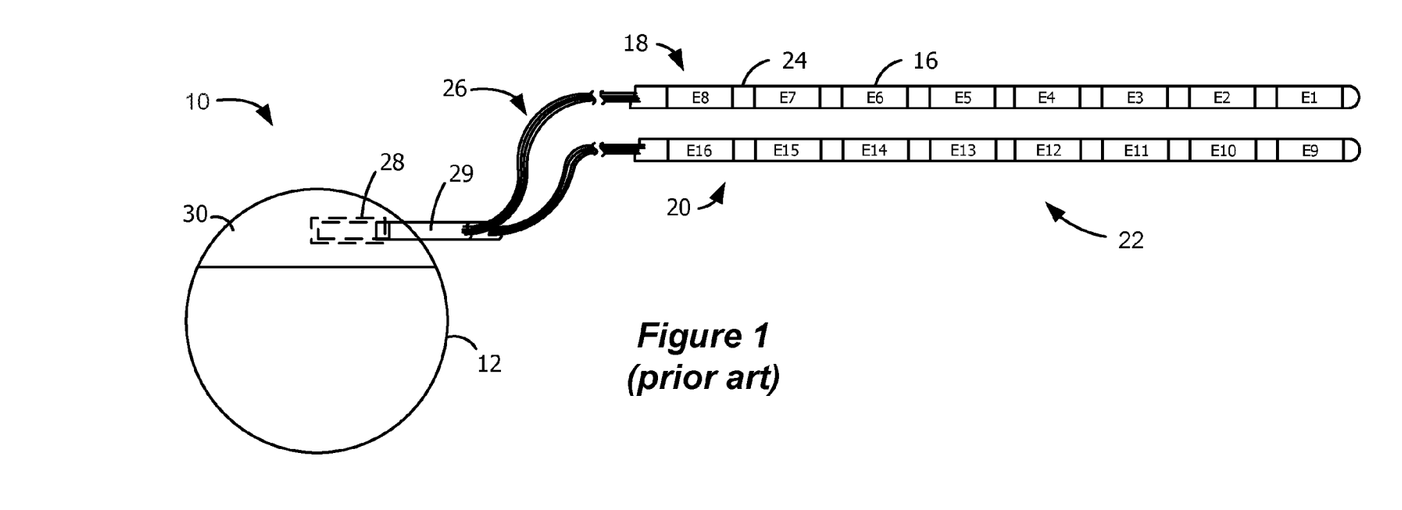
FIG. 1 shows an implantable medical device, specifically an Implantable Pulse Generator (IPG) in accordance with the prior art.

As shown in FIG. 1, a SCS system typically includes an Implantable Pulse Generator (IPG) 10, which includes a biocompatible device case 12 formed of a conductive material such as titanium for example. The case 12 typically holds the circuitry and battery 14 necessary for the IPG to function. The IPG 10 is coupled to distal electrodes 16 designed to contact a patient's tissue. The distal electrodes 16 are coupled to the IPG 10 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on lead 18, labeled $E_1$-$E_8$, and eight electrodes on lead 20, labeled $E_9$-$E_{16}$, although the number of leads and electrodes is application specific and therefore can vary. The leads 18, 20 contain proximal electrode contacts 29, which couple to the IPG 10 using lead connectors 28 fixed in a non-conductive header material 30 such as an epoxy.

Figure 2A:
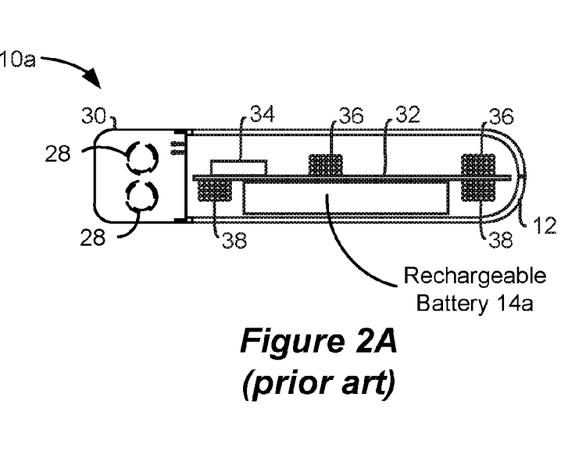
FIGS. 2A and 2B show a rechargeable-battery IPG and a primary-battery IPG respectively in accordance with the prior art.
Figure 2B:
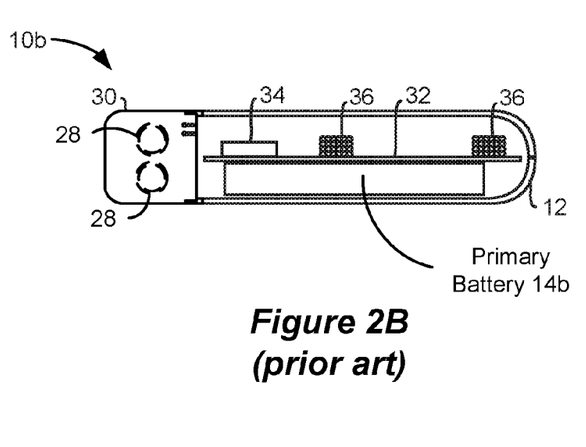

As shown in the cross-sections of FIGS. 2A and 2B, an IPG 10 typically includes an electronic substrate assembly including a printed circuit board (PCB) 32, along with various electronic components 34 mounted to the PCB. A telemetry coil 36 is used to transmit/receive data to/from an external controller (not shown). In these examples, the telemetry coil 36 is within the case 12, as disclosed in U.S. Pat. No. 8,577,474, although it can also be placed in the header 30 in other examples.

Figure 3:
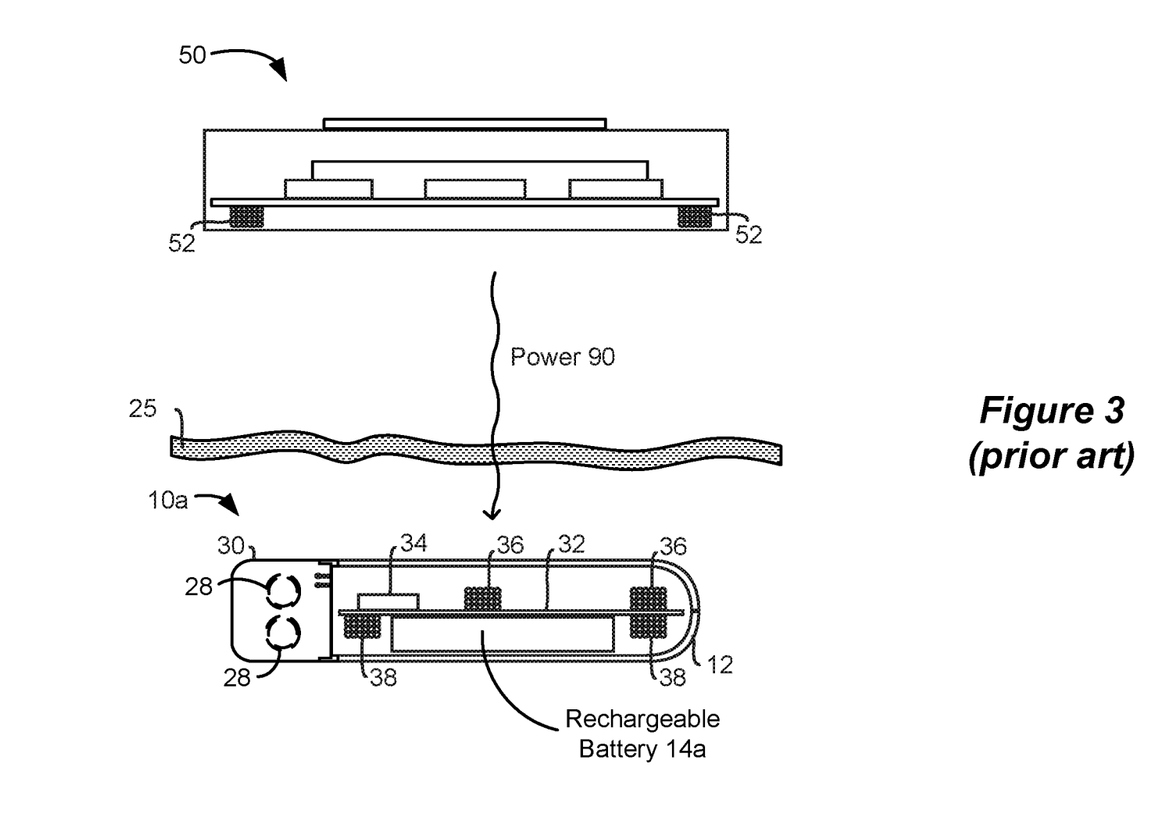
FIG. 3 shows an external charger used to recharge the battery in the rechargeable-battery IPG in accordance with the prior art.

IPGs can differ in the type of battery 14 employed. FIG. 2A shows an IPG 10a that contains a rechargeable secondary battery 14a. To facilitate recharging of battery 14a, the IPG 10a contains an additional charging coil 38. As shown in FIG. 3, charging coil 38 allows an external charger 50 to provide power 90 to recharge the battery 14a when necessary. As one skilled in the art will understand, such means of charging battery 14a using an external charger 50 occurs transcutaneously via magnetic induction: the external charger 50 is turned on, and an AC current is generated in coil 52 in the external charger. This produces an AC magnetic field 90, which induces an AC current in charging coil 38 in the IPG 10a. This current is rectified to a DC level in the IPG 10a, and used to recharge the battery 14a. Rechargeable batteries 14a can be formed using different chemistries, but lithium ion polymer batteries are popular for use in implantable medical devices, and produce voltages of about 4.2 Volts.

FIG. 2B, by contrast, shows an IPG 10b that contains a non-rechargeable primary battery 14b, i.e., one in which the electrochemical reaction is not reversible by passing a charging current therethrough. Because battery 14b is not rechargeable, there is no need for a charging coil (compare 38 in FIG. 2A) in IPG 10b. However, primary batteries use up the materials in one or both of their electrodes, and thus have a limited life span. Once the battery 14b is exhausted, it will be necessary to explant IPG 10b from the patient, so that the battery 14b can be replaced and the IPG 10b re-implanted, or so that a new IPG 10b with a fresh battery 14a can be implanted. Primary batteries 14b can be formed using different chemistries, but Lithium CFx batteries, or Lithium/CFx-SVO (Silver Vanadium Oxide) hybrid batteries are popular for use in implantable medical devices, and produce voltages of 1.2-3.2 Volts.

It is easy to assume that a patient should always be provided an implant with a rechargeable battery to permit charging when needed without the need of explantation, but there are also good reasons to prefer an implant with a non-rechargeable primary battery. Primary batteries are typically cheaper than rechargeable batteries, and may not suffer from reliability concerns inherent with rechargeable batteries. Moreover, use of a primary battery in an implant saves costs in other ways: the implant need not contain the overhead of a charging coil (38, FIG. 2A), and an external charger 50 (FIG. 3) can be entirely dispensed with. Moreover, the patient is convenienced by having an implant with a primary battery, as she will not have to concern herself with charging it. The case of a primary-battery implant may also be smaller than a rechargeable-battery implant, which would also convenience the patent.

As the inventors recognize, a clinician currently has little guidance to know in advance whether a given patient would most likely benefit from having an implant with a rechargeable battery 14a, or from having an implant with a primary battery 14b. This disclosure provides solutions.

DETAILED DESCRIPTION

As noted earlier, it is not always clear to a clinician whether a given patient would benefit from having an implant with a rechargeable or primary battery. The inventors realize that, at least in the context of an IPG, information can be discerned from the external trial stimulation phase to assist the clinician in making this determination.

Figure 4:
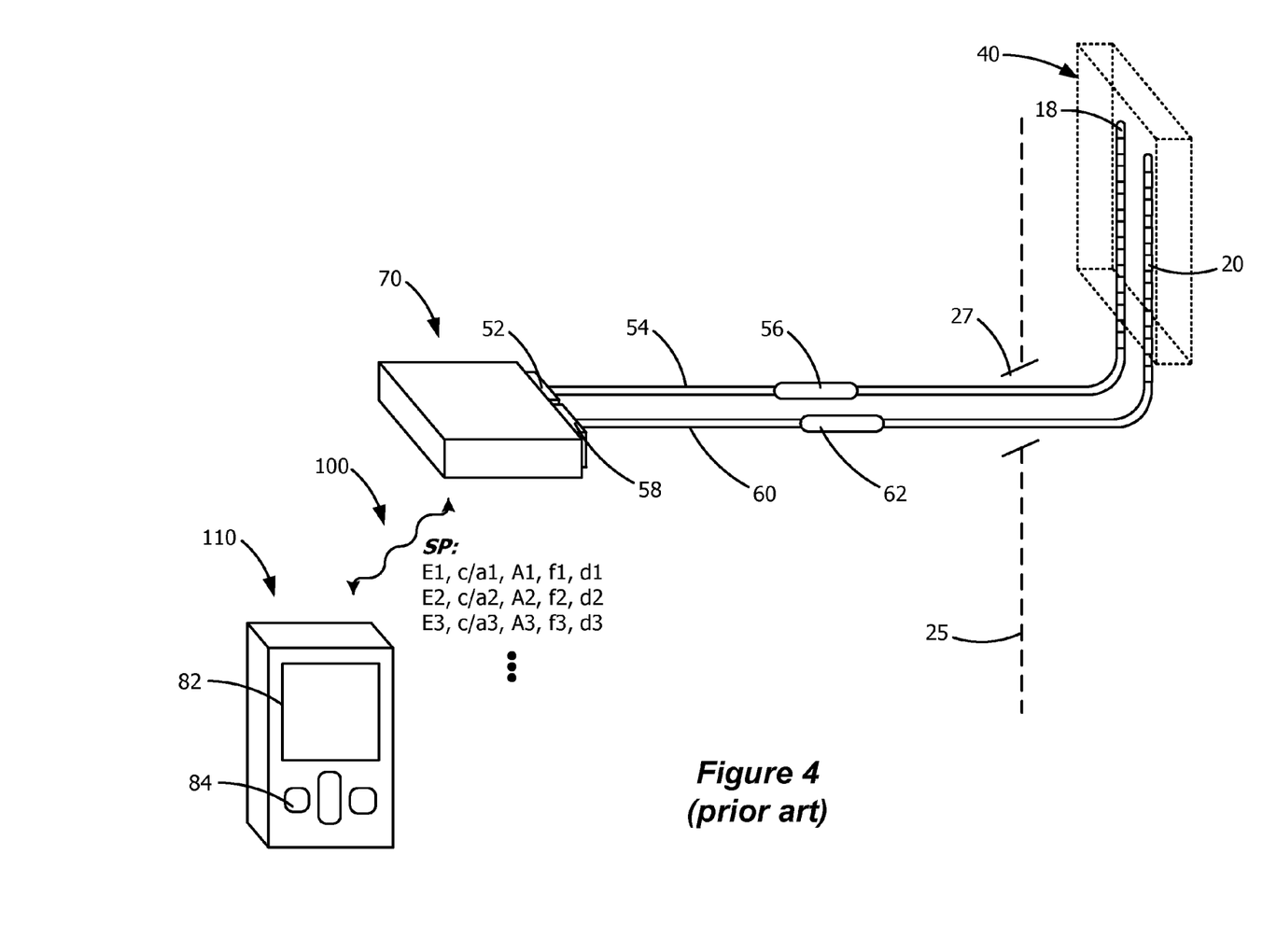
FIG. 4 shows an external trial stimulator (ETS) used prior to implantation of an IPG, and an external controller in communication with the ETS, in accordance with the prior art.

The external trial stimulation phase precedes actual implantation of the IPG, and is shown in FIG. 4. As shown, the patient at this stage has had electrode leads 18 and 20 implanted into her spinal cord 40 by the clinician. As is typical, the leads 18 and 20 are implanted on right and left sides of the spinal cord 40 to allow the IPG 10 flexibility to recruit and stimulate different nerves that may be causing the patient's pain or other symptoms. After implantation of the leads 18 and 20, the proximal ends of the leads protrude through the patient's skin 25 via an opening 27.

The patient is provided with an external trial stimulator (ETS) 70, which is coupled to the implanted leads 18 and 20 via lead extensions 54 and 60. These lead extensions 54 and 60 couple to the ETS 70 via connectors 52 and 58, and couple to the leads 18 and 20 via lead acceptors 56 and 62, which like lead connectors 28 (FIG. 1) are designed to accept the proximal electrode contacts 29 of the leads 18 and 20 (FIG. 1). As such, the lead extensions 54 and 60 contain at least the same number of wires as there are electrodes on each lead. The external trial simulator 70 can then be affixed to the patient in a convenient fashion for the duration of the external trial stimulation phase, which may last for two or so weeks for example. Typically, the external trial simulator 70 is placed into a belt to be worn by the patient.

The ETS 70 provides stimulation to the patient in much the same way as the IPG eventually will once it is implanted. Essentially, the ETS 70 mimics operation of the IPG, so that therapy can be tried and adjusted prior to actual implantation of the IPG. Therapy typically comprises a stimulation program (SP) specifying a number of stimulation parameters, such as which electrodes are selected for stimulation; whether such active electrodes are anodes or cathodes (c/ax); the magnitude of the stimulation (e.g., current; Ax) at the active electrodes; and the frequency (fx) and duration (dx) of stimulation at the active electrodes, assuming such stimulation comprises stimulation pulses as it typical. As shown in FIG. 4, the stimulation program is shown defining each of these stimulation parameters for each of the electrodes, but a stimulation program could be represented more simply. For example, if a particular electrode's amplitude is specified as Ax=0, then it will be understood that that electrode is not active, and that other parameters for that electrode (e.g., c/ax, fx, dx) are irrelevant or ignored.

The stimulation program used during the external trial stimulation phase can be modified wirelessly to try and determine effective therapy for the patient. As shown in FIG. 4, such control can be provided an external controller 110 which wirelessly 100 adjusts the stimulation program provided by the ETS 70 to the patient. The external controller 110 and the external trial stimulation 110 are thus both be provided with wireless telemetry means (e.g., antennas, transceiver circuitry) to facilitate such wireless communications 100, which may take place using any suitable telemetry scheme and hardware. As shown, the external controller 110 may include a user interface for the clinician, including a display screen 82 and touchable buttons 84 which the clinician can use to modify the stimulation program and to transmit it to the ETS 70.

The external controller 110 as shown is hand-held and portable, and thus is similar to external controllers used by patients to adjust their stimulation programs. See, e.g., U.S. Pat. No. 8,498,716; U.S. Patent Application Publication 2012/0101551. However, the external controller 110 can also take the form of a clinician's programmer of the type used by clinicians either in their offices or in an operating room environment. Generally speaking, the external controller 110 can comprise any suitable computer apparatus, such as a desk top computer, a lap top computer, a tablet computer, etc. As such, the user interface of the external controller 110 (e.g., display 82; buttons 84) can be separated from its computing and communication hardware, and thus the external controller 110 need not comprise an integrated device housing all necessary components as shown. Additionally, while it is convenient that the external controller 110 and ETS 70 communicate wirelessly 100, they may also be physically linked by cabling. The ETS 70 usually contains a battery within its housing to provide the power necessary to implement the stimulation program and to provide the prescribed stimulation at the electrodes 16.

If a suitable stimulation program relieving the patient's symptoms is determined during the external trial stimulation phase, this may suggest that implantation of an IPG is warranted. An IPG is thus implanted in the patient (typically in the patient's upper-buttock area), and the leads 18 and 20 are tunneled though the patient's tissue to connect the proximal electrode contacts 29 to the lead connectors 28 in the IPG's header 30. Moreover, the stimulation program determined during the external trial stimulation phase can be wireless telemetered to the IPG (via telemetry coil 36; FIGS. 2A and 2B) after implantation, which should give the patient a basis for effective therapy, which can be wirelessly adjusted later by the patient using a patient external controller, as described above.

By contrast, if no suitable stimulation program is determined during the external trial stimulation phase, or if the patient experiences troubling side effects, this may suggest that neurostimulation will be ineffective for that patient. In this case, an IPG is not implanted, and the leads 18 and 20 are explanted. Alternatively, the implantation of the leads 18 and 20 may be adjusted by the clinician via further surgery, and the external trial stimulation period extended to see if a suitable stimulation program can then be determined. In short, external trial simulation allows the effectiveness of therapy to be vetted before subjecting the patient to the inconvenience of implantation of the IPG, and the possible need to explant the IPG if successful therapy cannot be achieved.

The inventors recognize that information gleaned during the external trial stimulation phase can assist a clinician in deciding whether a patient would best benefit from receiving an IPG 10a having a rechargeable battery (FIG. 2A), or an IPG 10b having a primary battery (FIG. 2B).

Figure 5:
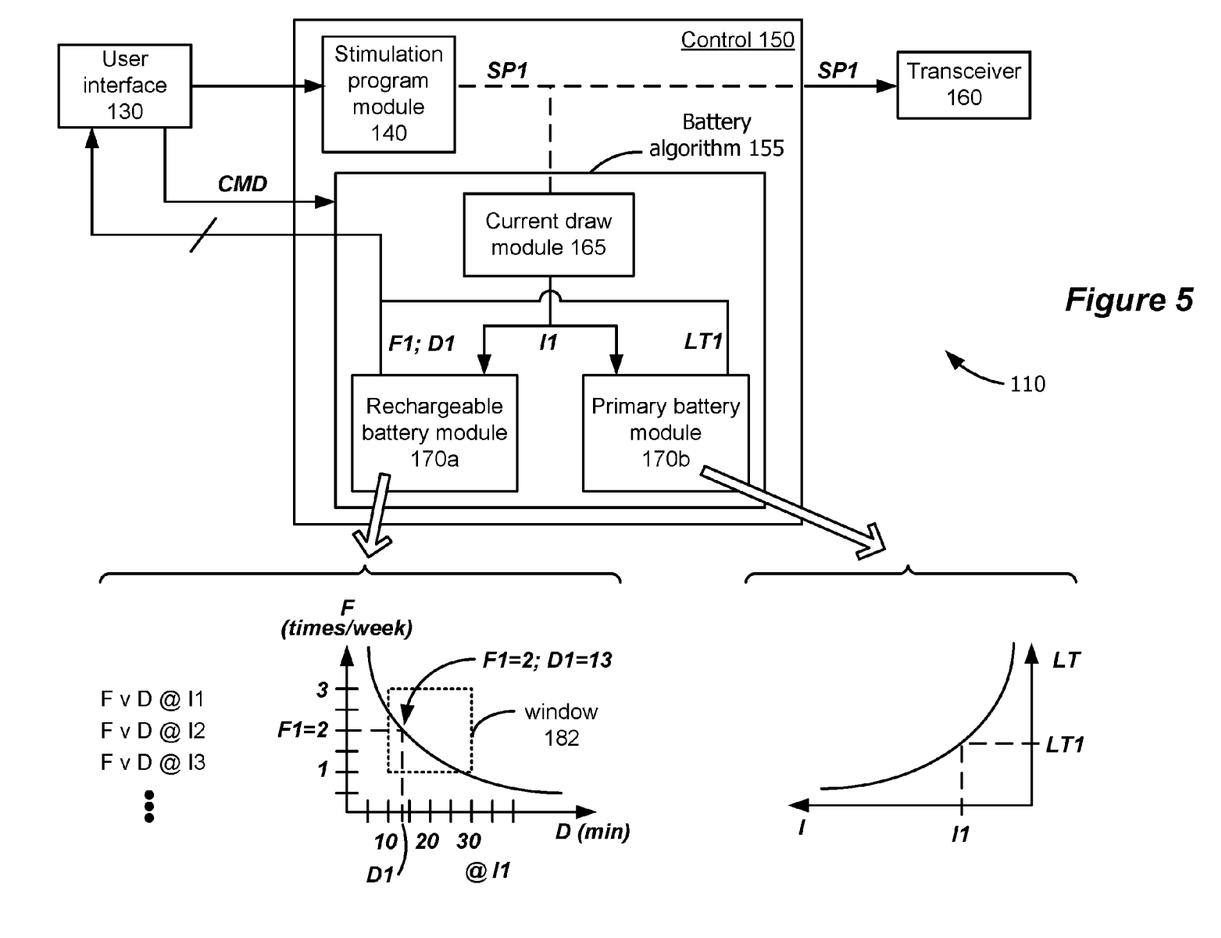
FIG. 5 shows an improved external controller including a battery algorithm able to estimate battery performance parameters for a rechargeable-battery IPG and a primary-battery IPG during an external trial stimulation phase, and to optionally automatically recommend to a clinician which IPG would be best suited for implantation in the patient.
Figure 6A:
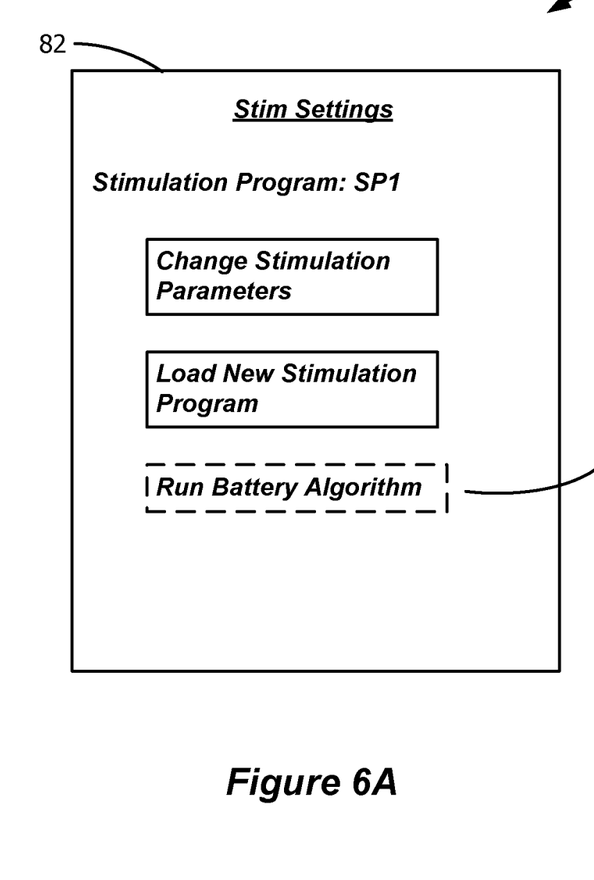
FIG. 6A shows the user interface of the improved external controller including the option to run the battery algorithm.

FIG. 5 shows a block diagram of the circuitry for an improved external controller 110 to assist the clinician in making this primary-battery versus rechargeable-battery determination. As shown, the external controller 110 includes a user interface 130, such as the display 82 and buttons 84 mentioned earlier. Using the user interface 130, the clinician can modify the stimulation program for a given patient. For example, as shown in FIG. 6A, the clinician can select displayed options to either change specific stimulation parameters (electrode, polarity, amplitude, frequency, duration, etc.) for the stimulation program that is currently running, or can load another stimulation program previously stored in the external controller 110.

Referring again to FIG. 5, the user interface 130 interfaces with a stimulation program module 140 to form, or retrieve from memory, the stimulation program resulting from these selections. Stimulation program module 140 can be associated with, or reside in, control circuitry 150 within the external controller 110, which may comprise a microcontroller for example, or other assortments of logic blocks, including memory. Transceiver circuitry 160 wirelessly transmits the stimulation program SP1 to the ETS 70 as described earlier. Alternatively, transceiver circuitry 160 need not be wireless and can send and/or transmit information to and from the ETS 70 via a wired connection, as also noted earlier. The ETS 70 then executes this stimulation program SP1 to provide therapy to the patient, and when the patient reports good relief from symptoms, then this stimulation program SP1 is assumed optimal, and would likely be stored within the external controller 110. Storing optimal stimulation program SP1 will be useful, as mentioned earlier, so that it can be wirelessly transmitted to the IPG 10a or 10b once it is eventually implanted in the patient.

After determining an optimal stimulation program SP1 for the patient, the question remains whether the patient would best benefit from having a primary battery IPG 10a or a rechargeable battery IPG 10b implanted. To assist the clinician in making this determination, and referring again to FIG. 6A, an option is provided to run a battery algorithm, which when selected (CMD; FIG. 5) will present the clinician estimations regarding the power performance of both types of IPGs, as well as an optional automated recommendation as to which might be most appropriate for the patient. Battery algorithm may also run automatically when a stimulation program is changed for example, and without the need for selection at the user interface 130.

Figure 7:
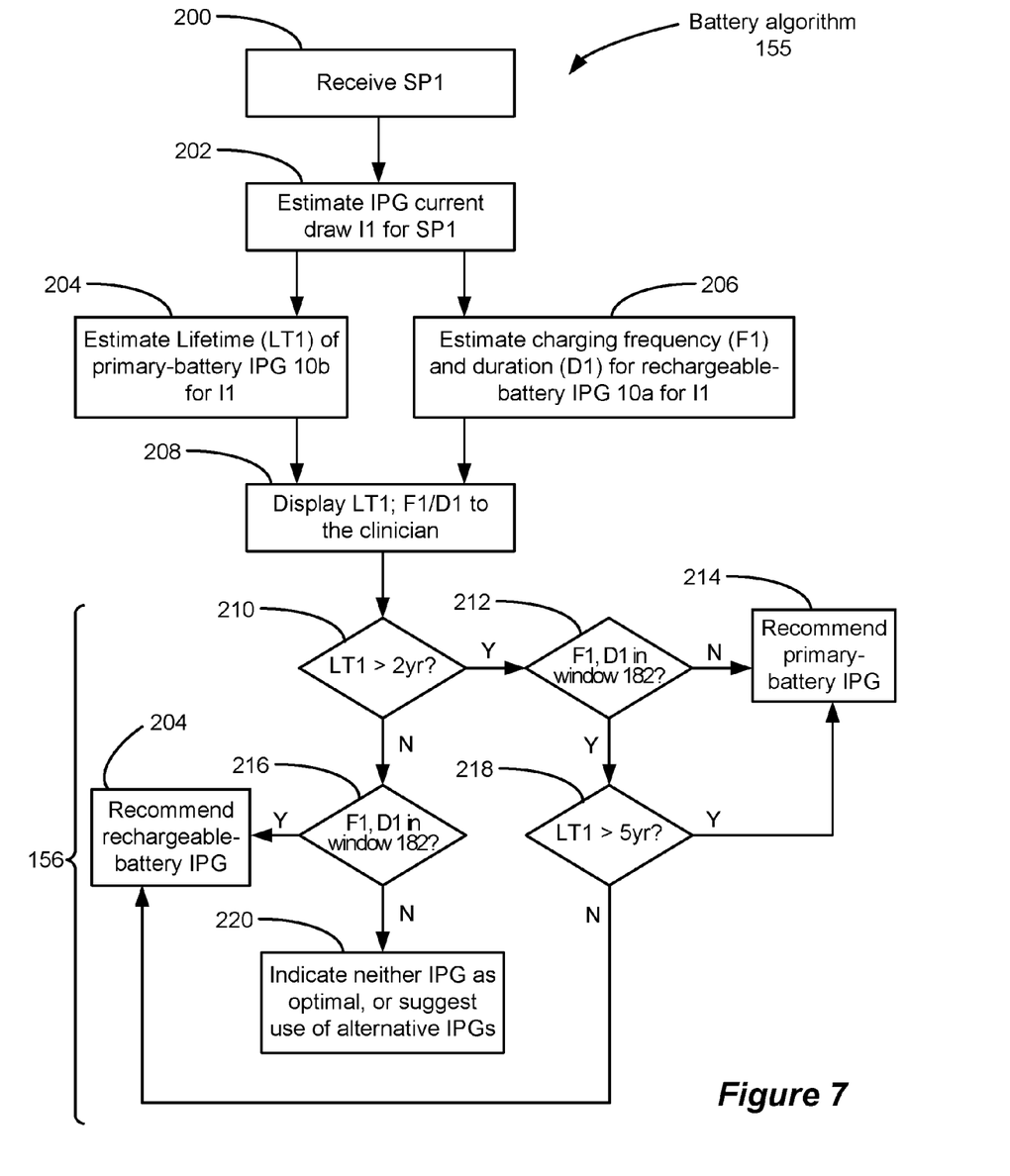
FIG. 7 shows a flow chart of one example of the battery algorithm.

When the clinician selects to run the battery algorithm (or it otherwise automatically operates), and referring again to FIG. 5, the battery algorithm 155 associated with the control circuitry 150 operates, which is also illustrated in flow chart form in FIG. 7. As a first step, the algorithm 155 receives the optimal stimulation program SP1 (FIG. 7, 200). A current draw module 165 then estimates the expected current draw I1 resulting from that stimulation program, i.e., the current that the IPG would be expected to draw were it running the stimulation program SP1 (FIG. 7, 202). I1 may also represent information indicative of the expected current draw, and could comprise an expected power draw (in Watts) for example.

To implement this function, current draw module 165 is programmed with information regarding the expected operation of the circuitry of the IPG to be implanted, which may be the same (apart from the battery) for IPGs 10a and 10b, and which also may be the same as the circuitry in the ETS 70 as noted earlier. Thus, current draw module 165 can determine I1 based on the number of active electrodes, the amplitude (A) of the current at those electrodes, the duration (d) of the current pulses and their frequency (f)—i.e., the stimulation parameters of stimulation program SP1. Such information can be based on simulations of the circuitry in the IPG, or from experimental measurements taken from the circuitry of an example IPG. One skilled in the art will realize that how the current draw modules 165 determines I1 can vary and can be based on a number of assumptions. For example, assume the current draw module 165 is programmed to understand that stimulation pulses with an amplitude A, a duration d, and a frequency f will draw 1 mA in the IPG. If the stimulation program SP1 instead defines pulses with a combined amplitude of 0.6 A, duration 1.3d, and frequency 0.7f, the current draw module 165 can determine that I1 would be 0.6*1.3*0.7*1 mA. One skilled will realize that there could be other ways for determining or estimating I1 in current draw module 165.

Once current draw I1 is determined, the algorithm 155 then passes this value to a rechargeable battery module 170a and to a primary battery module 170b. These modules 170a and 170b are respectively programmed with information regarding the expected operation of battery 14a in rechargeable battery IPG 10a and battery 14b in primary battery IPG 10b. As the differences in batteries 14a and 14b warrant, modules 170a and 170b seek to determine different information for both types of IPGs relevant to the clinician's decision as to which should be implanted.

Rechargeable battery module 170a provides the clinician information regarding how often the rechargeable battery 14a in IPG 10a would need to be recharged using external charger 50 (FIG. 2) assuming the IPG draws I1 of current. More specifically, module 170a informs the clinician of the expected duration (D) of each charging session and the frequency (F) of such charging sessions. These parameters are relevant to consider because they impact the patient, who will ultimately be responsible for using the external charger 50 to charge the battery 14a.

Determining charging duration D and frequency F can be based on simulation or experimental results regarding how efficiently or quickly the external charger 50 recharges battery 14a. For example, rechargeable battery module 170a can be programmed assuming a particular coupling or alignment between the external charger 50 and the IPG 10a. This assumption may comprise a "worst case" in which alignment between the external charger 50 and the IPG 10a is deemed suitable for charging the IPG 10a's battery 14a, but is nonetheless not optimal.

Generally speaking, the frequency of charging (F) and the duration of charging (D) are inversely proportional, and both parameters are directly proportional to I1. As such, rechargeable battery module 170a can be programmed with information of the relationship between frequency (F) and duration (D) at various current draws (I). The determined power draw I1 can be used to "look up," or interpolate, an appropriate relationship between F and D, as shown in the graph at the bottom left of FIG. 5. This graph shows the inverse relationship between F and D for the determined current draw I1, and further shows a window 182 of acceptable values for both F and D. Such acceptable values for window 182 are subject to designer preferences perhaps based on patient feedback; for example, a patient may not want to have to recharge their IPG 10a more than three times a week, and may desire that the duration of charging not be too short or too long. In the example shown, it is assumed that a patient would only desire to recharge IPG 10a between 1 and 3 times a week (i.e., 1/week<F<3/week), and that duration of charging should be between 10 and 30 minutes (i.e., 10 min<D<30 min).

With window 182 set in this manner, rechargeable battery module 170a thus seeks to determine logical values to report to the clinician regarding battery 14a's expected recharging performance. Because charging is logically viewed by the patient as occurring a set number of times daily, it is generally desired to provide the clinician an integer value for the charging frequency F, which again could only comprise 1, 2, or 3 charging sessions per week in accordance with the constraints defined earlier for the window 182. The rechargeable battery module 170a then assesses whether a charging duration D appears within window 182 at any of these values for F. In the example graph shown, only F1=2 provides a duration D1 within the window 182—specifically D1=13 minutes at F1=2 charging sessions per week—and thus such values comprise estimated battery performance parameters for rechargeable-battery IPG 10a (step 206; FIG. 7). As such, this information will be reported to the clinician, as described in further detail later.

If more than one value for D appears in the window 182 for an acceptable value for F, then rechargeable battery module 170a may decide which would be the most appropriate to report to the clinician. As a default, and to provide an indication assumedly most convenience to the patient, the result having the lowest value for F (and its corresponding D) may be provided to the clinician. This is not strictly necessary, and instead the lowest value for D (and its corresponding F) could be provided instead. All values for F and D appearing within the window 182 could also be reported.

Primary battery module 170b by contrast is not concerned with recharging particulars, but is instead concerned with determining how long the primary battery 14b in IPG 10b can be expected to function given the estimated current draw I1. In this regard, the primary battery module 170b is programmed with the capacity (C) of the battery 14b, which is normally expressed in amp-hours. Knowing the capacity and the estimated current draw, the lifetime (LT1) of the battery 14b can be estimated (LT1=C/I1), which is shown graphically at the bottom right of FIG. 5 (step 204; FIG. 7). Alternatively, an index indicative of the lifetime of the battery 14b could also be determined and interpreted by the clinician.

Figure 6B:
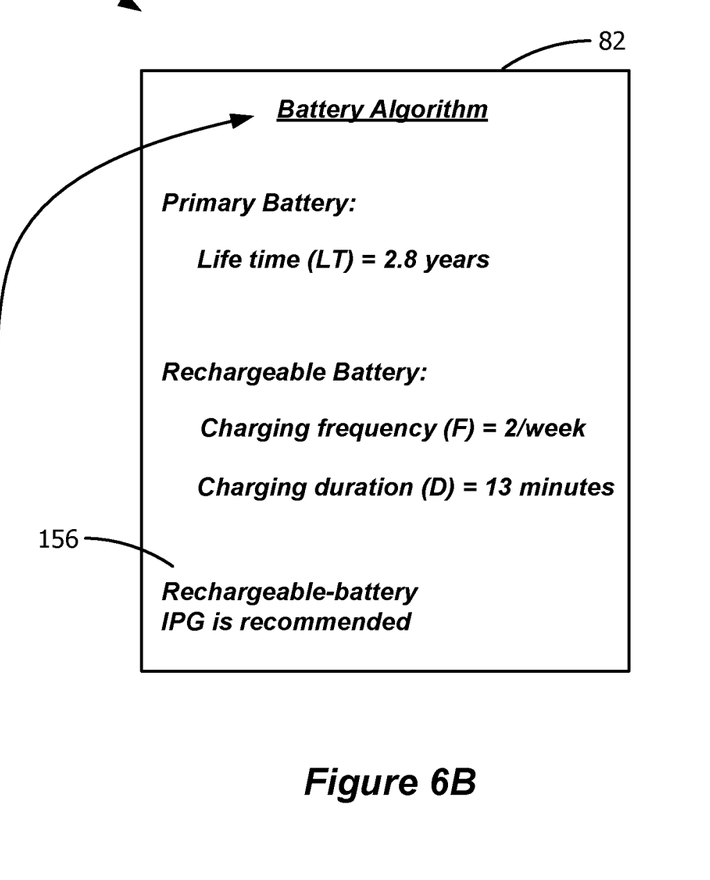
FIG. 6B shows the output of that algorithm as provided to the clinician.

Once these battery performance parameters (LT1, F1, D1) have been determined by modules 170a and 170b, they can be provided to the clinician via the user interface 130 of the external controller 110 (step 208; FIG. 7), as shown in FIG. 6B. Modules 170a and 170b, like module 165, are shown as part of the control circuitry 150 in the external controller 110, and may comprise firmware or microcode in the control circuitry. However, this is not strictly necessary, and instead such modules can be stored in memory circuitry communicating with control circuitry 150.

As also shown in FIG. 6B, the battery algorithm 155 can optionally act further to provide a recommendation 156 to the clinician as to which IPG 10a or 10b would be best for the patient given the reported battery performance parameters. Recommendation 156 can be automatically generated in accordance with logic programmed into the algorithm 155, and one simple, non-limiting example is shown in FIG. 7. In the example shown, algorithm 155 first determines whether the estimated lifetime LT1 of the primary battery 14b meets a minimum time threshold, such as two years, which threshold might be chosen as a minimum acceptable time interval for explant of a depleted primary-battery IPG 10b and re-implantation of fresh IPG 10b (step 210). If this threshold is exceeded, the battery performance parameters of rechargeable-battery IPG 10a (F1, D1) are assessed to see if any are within the window 182 (step 212) defined earlier. If not, a rechargeable-battery IPG 10a may not be acceptable as it would be inconvenient for the patient to charge, and hence the primary-battery IPG 10b (whose lifetime LT1 is minimally acceptable) is recommended (step 214). If F1 and D1 are in the window 182, suggesting that the rechargeable-battery IPG 10a is also acceptable, the lifetime of the primary-battery IPG 10b is again assessed to see if its lifetime exceeds a maximum time threshold, such as 5 years (step 218). This threshold might be chosen as a lifetime so significant that the primary-battery IPG 10b would necessarily be recommended (step 214), even if the rechargeable-battery IPG 10a might also be acceptable. By contrast, if the maximum lifetime threshold for the primary-battery IPG 10b is not exceeded (step 218), the rechargeable-battery IPG 10a may be chosen (step 204), which as well as being acceptable may be expected to last for well over five years.

Returning to step 210, if the estimated lifetime LT1 does not exceed the minimum time threshold, the battery performance parameters of rechargeable-battery IPG 10a (F1, D1) are assessed to see if any are within the window 182 (step 216). If so, the rechargeable-battery IPG 10a may be chosen (step 204). If not, this may indicate that neither of the IPGs 10a or 10b are acceptable, perhaps because the estimated current draw I1 is so significant that a primary-battery IPG 10b would be depleted too quickly, and that a rechargeable-battery IPG 10a would require an inordinate amount of recharging. Hence, the clinician may be notified of this fact (step 220), or may alternatively be suggested to consider a different IPG, perhaps one having a larger capacity primary or rechargeable battery.

The automated recommendation steps in the battery algorithm 155 could also include assessment of different factors, such as the life expectancy or age of the patient, which might play into or modify whether certain of the battery performance parameters are acceptable or can be tolerated.

Figure 8:
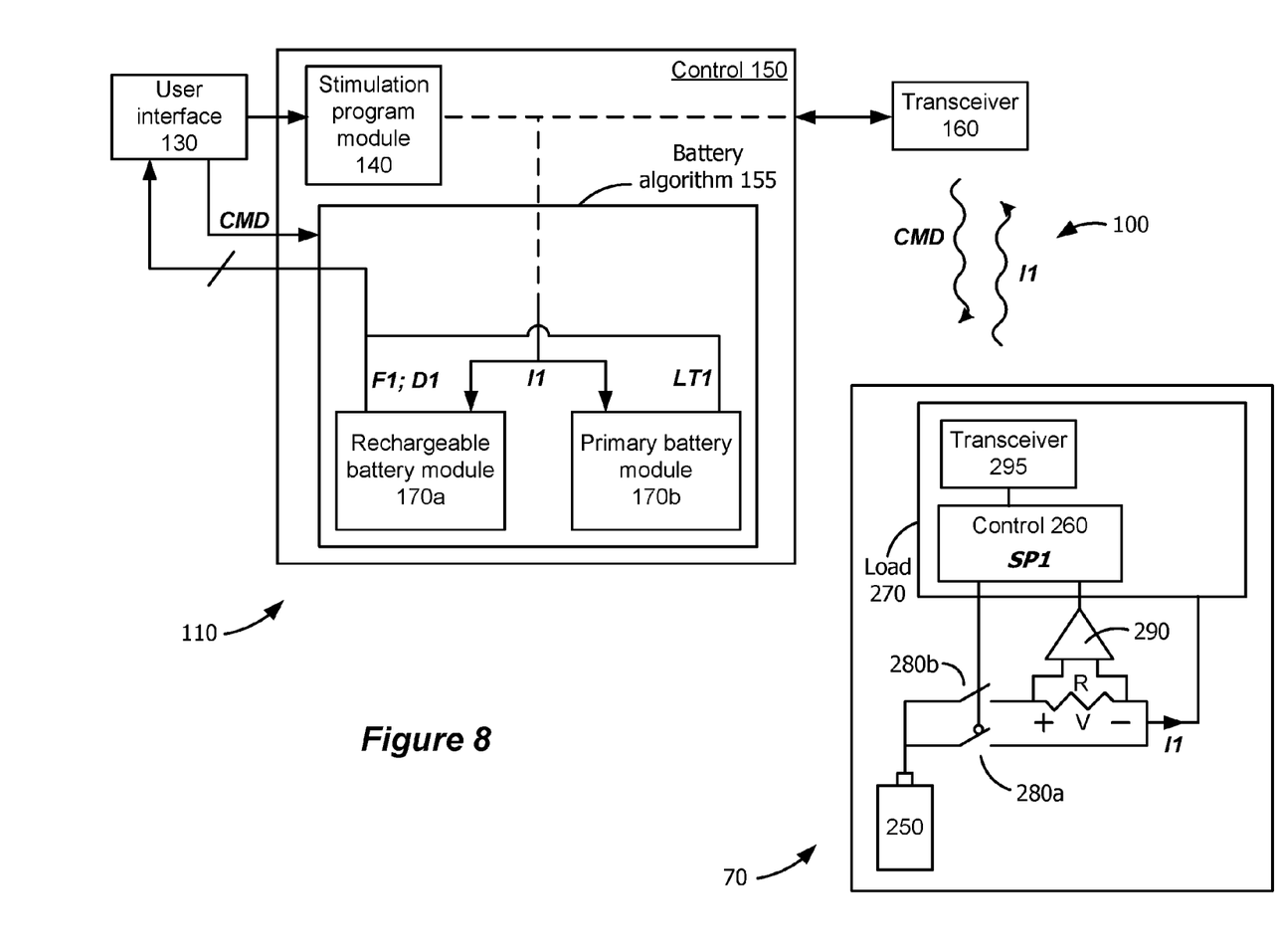
FIG. 8 shows a modification in which the ETS provides current draw information to the battery algorithm in the improved external controller.

FIG. 8 shows a modification to the above technique in which battery performance parameters are determined based on information sent or telemetered from the ETS 70. In this alternative, the expected current draw I1 is not estimated at the external controller 70 based on a stimulation program SP1 as occurred earlier. Instead, the expected current draw I1 is measured in the ETS 70 as it executes stimulation program SP1. This is a useful means for determining the current draw I1 in the to-be-implanted IPG for a given stimulation program SP1, especially if the circuitry in the ETS is made to match the circuitry in IPGs 10a or 10b, as is often the case.

This can involve minor modification to the circuitry of the ETS 70, which normally comprises a battery 250 and the load 270 that it powers. Load 270 includes all of the circuitry within the ETS 70, including the biasing circuitry for driving currents to the electrodes pursuant to SP1 (not shown), control circuitry 260, and transceiver 295 for wirelessly communicating with the external controller 110, all of which can again be the same as what is present in IPGs 10a and 10b. Added to the ETS 70 is circuitry designed to measure the current draw I1 in ETS 70, including switches 280, a measuring resistor R, and a differential amplifier 290. Other current draw measuring circuitry could be used as well; this is merely one example.

When the clinician selects to run the battery algorithm 155 (FIG. 6A), control circuitry 150 in the external controller 110 generates a command (CMD) which is wirelessly broadcast to the ETS 70, which in turn measures the current drawn I1. This occurs in the depicted example by controlling switches 280a and 280b. During normal operation of the ETS 70 (i.e., when CMD hasn't been received at the ETS 70), switch 280a is closed and switch 280b is opened, and hence the ETS battery 250 can deliver the current draw I1 to the load 270 so that it is powered normally. When command CMD is received, switch 280b is closed and switch 280a is opened, which places resistor R in line with the current draw I1. This causes a small voltage (V) to drop across resistor R, which is detected by the differential amplifier 290. Because the value of R is known, the current draw I1 can be determined (V/R) by control circuitry 260, and telemetered back to the external condoler 110. Note that the current draw in the ETS 70 (and the eventual IPG 10a or 10b that replaces it) may not be constant, particularly if the ETS is issuing pulses. As such, it may be necessary to measure the voltage drop over a significant time period, such as several pulse periods, to get an accurate or averaged understanding of the current draw, I1.

Once received by the external controller 110, current draw I1 can be processed by algorithm 155 as before to determine the battery performance parameters (LT1, F1, D1), to display them to the clinician, and to recommend a proper IPG. Note in this alternative of the technique that current draw module 165 (FIG. 5) can be omitted, because current draw I1 is measured directly, and need not be inferred from the stimulation program SP1.

Figure 9A:
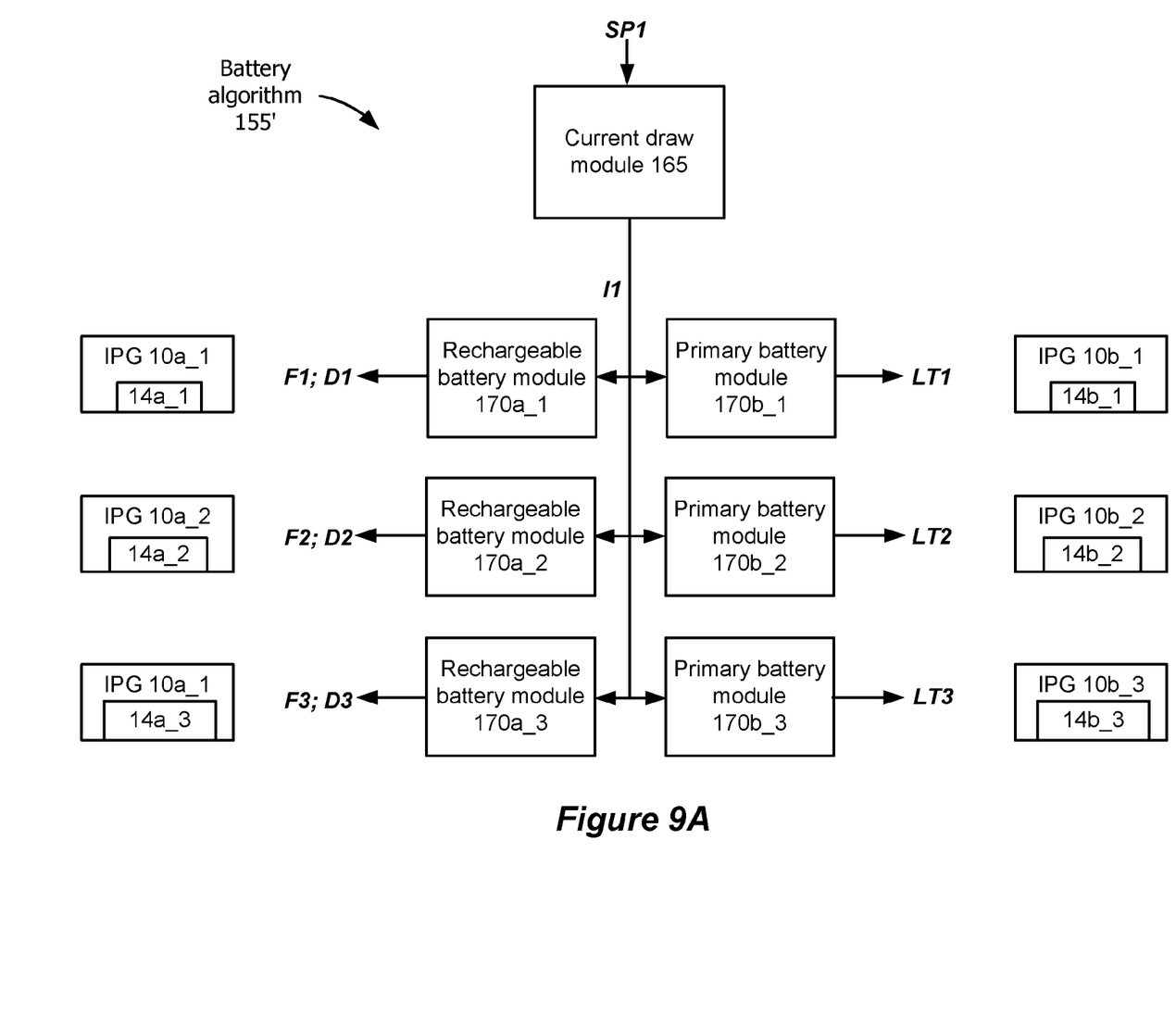
FIGS. 9A and 9B show a modification to the battery algorithm allowing the clinician to choose from more than one rechargeable-battery IPG and more than one primary-battery IPG.
Figure 9B:
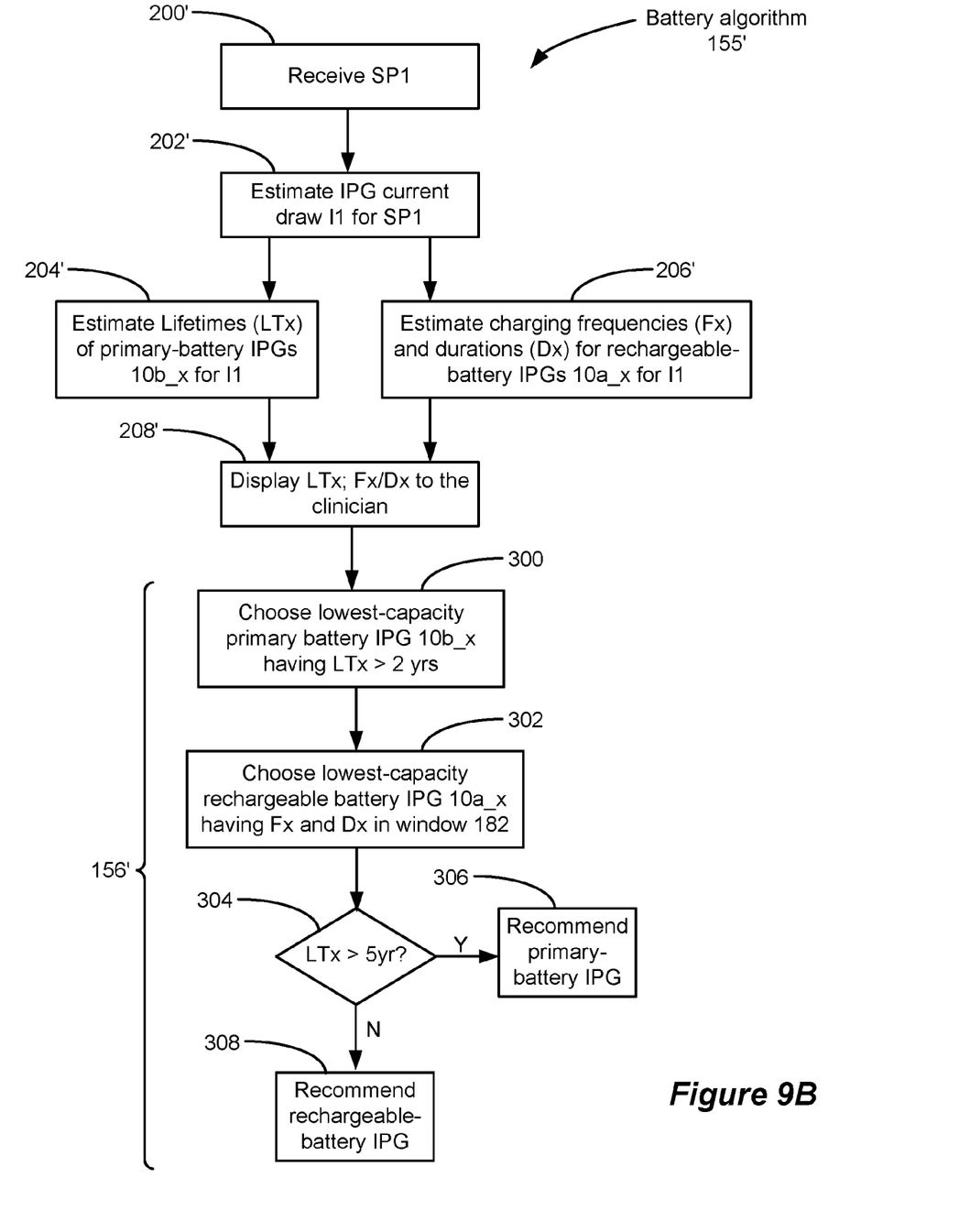

To this point in the disclosure it has been assumed that the disclosed technique has been used to assist the clinician in choosing for a given patient whether a rechargeable 10a or primary 10b IPG would be best for implantation. Further, it has been assumed that the operative circuitry in these IPGs 10a and 10b are the same (other than differences relating to their batteries 14 and 14b). However, the technique is not so limited, as depicted in FIGS. 9A and 9B. These figures illustrate a modification to the battery algorithm 155' in the external controller 110 in which more than two IPGs are selectable as possible candidates for implantation.

In FIG. 9A, it is assumed that the clinician can choose from three different rechargeable-battery IPGs (10a_1, 10a_2, 10a_3) each differing only in the capacity of their batteries (14a_1, 14a_2, 14a_3), and three different primary-battery IPGs (10b_1, 10b_2, and 10b_3) each differing again only in the capacity of their batteries (14b_1, 14b_2, 14b_3). It is further assumed that all IPGs otherwise have the same circuitry aside from their batteries, and that the IPGs with higher index numbers have higher battery capacities (e.g., battery 14a_2 has a higher capacity than battery 14a_1, etc.).

In this example, current draw I1 is again determined, and is sent to battery modules corresponding to each of the selectable IPGs. This yields additional battery performance parameters values (Fx, Dx, LTx) as shown.

Once these battery performance parameters are determined, the algorithm 155' can make a recommendation 156' of which IPG would be best suited for the patient, as shown in the flow chart of FIG. 9B. (Earlier steps in algorithm 155' should be clear from earlier discussions and aren't again discussed). The depicted automatic process for generating recommendation 156' in FIG. 9B is quite simple for example purposes, but could of course be much more complicated given the greater number of battery performance parameters it considers. Step 300 simply determines the lowest-capacity primary battery IPG 10b_x having an acceptable estimated lifetime LTx of greater than two years. This decision is based on the premise that a patient need not receive an IPG 10b_x of a greater capacity than is needed; this should reduce IPG cost and further may benefit the patient who may receive the smallest IPG 10b_x suitable for his needs. This minimum-capacity IPG 10b_x is chosen, and the others which might have too low or too high a capacity are excluded from the recommendation. Similar step 302 essentially does the same assessment for the rechargeable-battery IPGs 10a_x, determining the lowest-capacity rechargeable battery IPG 10a_x having acceptable power parameters Fx and Dx in the window 182 described earlier. This minimum-capacity IPG 10a_x is chosen, and the others which might have too low or too high a capacity are excluded from the recommendation. Then a decision is made as to which of the two remaining IPGs 10a_x and 10b_x should be chosen, which in the illustrated example simply turns on whether the estimated lifetime of the primary-battery IPG 10b_x is sufficiently long (>5 yrs; step 304) to warrant choosing that implant (step 306), and if not choosing the rechargeable-battery IPG 10a_x (step 308).

Algorithm 155' may consider other factors when providing a recommendation 156'. For example, algorithm 155' may not simply force a choice between the most logical of the rechargeable and primary-battery IPGs. Instead, other decisions may cause all of one type of IPG (e.g., all primary-battery IPGs 10b_x) to be excluded from the recommendation, with the final choice for recommendation occurring between two of the rechargeable-battery IPGs 10a_x.

Note the battery algorithm 155' can operate and be modified by wirelessly transmitting current draw I1 from the ETS 70, similar to what was described with reference to FIG. 8.

Figure 10:
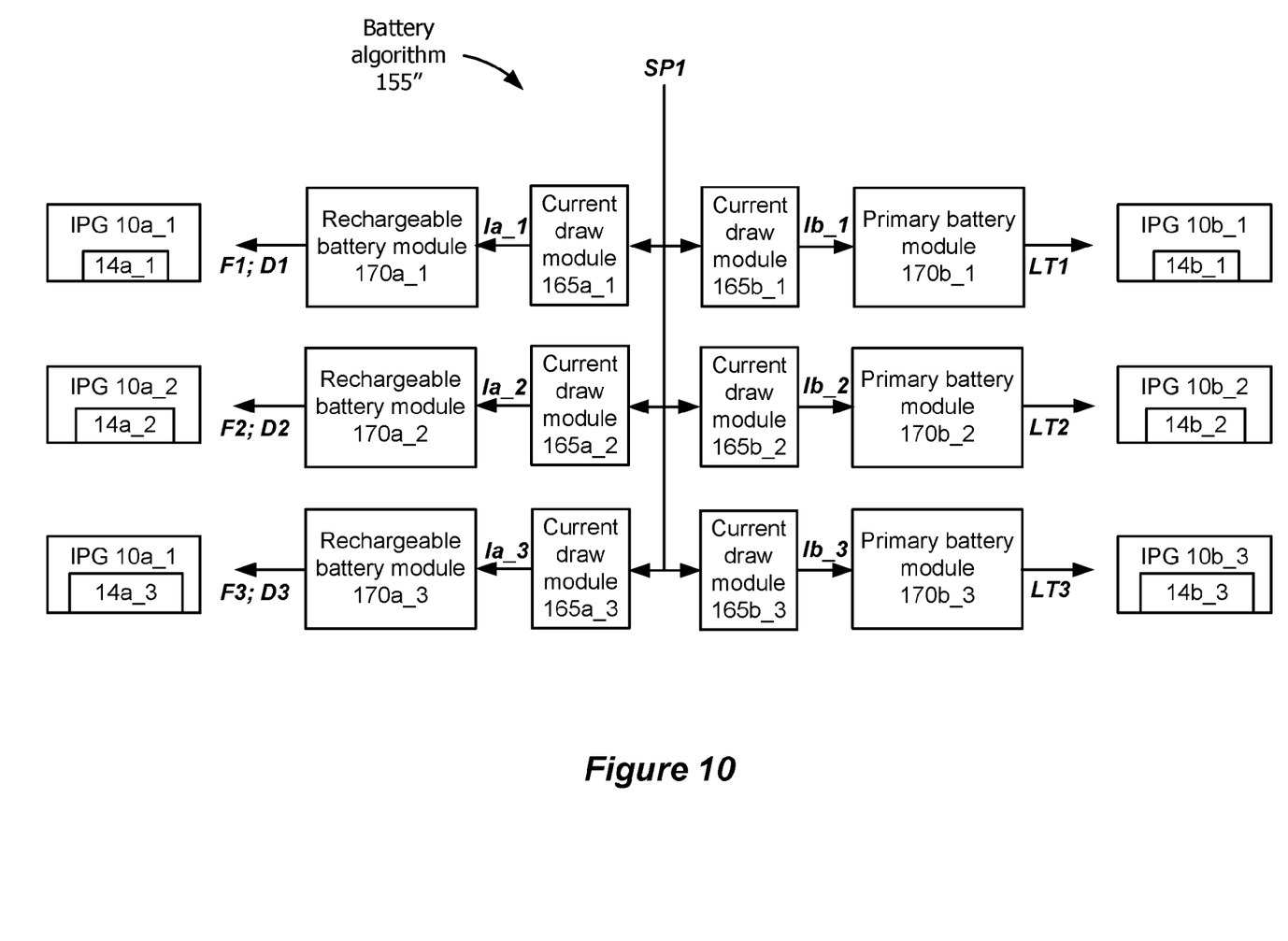
FIG. 10 shows another modification to the battery algorithm allowing the clinician to generically choose from multiple IPGs, even if their battery types and circuitries don't match, or even if their circuitries don't match the circuitry in the ETS.

FIG. 10 shows another modification to the battery algorithm 155", which like algorithm 155' allows the clinician to choose from three different rechargeable-battery IPGs (10a_1, 10a_2, 10a_3) and three different primary-battery IPGs (10b_1, 10b_2, and 10b_3). However, in this example, it is not assumed that the various IPGs have the same circuitry, nor is it assumed that the circuitry in the ETS 70 is the same as in any of the IPGs. In effect, algorithm 155" allows the clinician to generically assess and choose between any number of different IPGs available for implantation regardless of how different they might be and regardless of how different they may be from the ETS 70.

Because the circuitries in each of the IPGs may be different, a single current draw module 165 can't be used to predict a single current draw I1 applicable to all of the IPGs for a given stimulation program, as their unique circuitries may draw different amounts of current when executing that program. Instead, and as shown, the stimulation program SP1 is input to current draw modules 165a_x and 165b_x specifically programmed to estimate the current draw Iax or Ib_x of its corresponding IPG. Because the circuitry in each IPG may be different, the simulated or experimental data programmed into each current draw module 165 may be different.

For those IPGs having rechargeable batteries, the resulting Ia_x is input to a corresponding rechargeable battery module 170a_x, which as before is programmed with information regarding the expected operation of rechargeable batteries 14a_x for each rechargeable battery IPG 10a_x, which again may include assumption about how efficiently such batteries can be recharged by the external chargers. Each rechargeable battery module 170a_x outputs battery performance parameters Fx and Dx.

For the IPGs having primary batteries, the resulting Ib_x is input to a corresponding primary battery module 170b_x, which as before is programmed with information regarding the capacity of primary batteries 14b_x for each IPG 10b_x. Each primary battery module 170b_x outputs battery performance parameters LTx.

Once battery performance parameters Fx, Dx, and LTx are determined, they can be further considered by algorithm 155" to provide a recommendation 156', which may occur using the same steps of algorithm 155' discussed earlier (FIG. 9B). Thus, with the external controller 110 properly programmed, algorithm 155" allows the clinician to select the best IPG for the patient even though these IPGs may be different in their circuitries, their battery types (rechargeable versus primary), and their battery capacities.

While the external controller 110 and ETS 70 have been shown as separate, one skilled will understand that they could be combined into a single unit. That is, the ETS 70 could have its own user interface and be programmed with any of the disclosed battery algorithms to function as shown to assist a clinician. Moreover, one skilled will realize that while it is sensible that the disclosed technique operate on the external controller 110 normally used to communicate with the ETS 70, this is not strictly necessary. Instead, the external device used to run the battery algorithm and to display the output of that algorithm need not be the same device used to send stimulation programs to the ETS 70, so long as the external device running the battery algorithm is somehow otherwise made aware of necessary information from the external controller or the ETS.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
   an external stimulator configured to provide stimulation to a patient in accordance with an IMD stimulation program; and
   an algorithm configured to be programmable in control circuitry of an external device to assess a plurality of battery-powered IMDs implantable in a patient, wherein the algorithm is configured to determine at least one battery performance parameter for each of the plurality of IMDs at least in accordance with the stimulation program.

2. The system of claim 1, wherein the external stimulator is configured to be coupled to at least one lead implantable in the patient to provide the stimulation to the patient.

3. The system of claim 1, wherein the external stimulator is further configured to receive the stimulation program from the external device.

4. The system of claim 1, wherein the external stimulator is further configured to transmit the stimulation program to the external device.

5. The system of claim 1, wherein the algorithm is configured to indicate the at least one battery performance parameter for each of the plurality of IMDs to a user of the external device.

6. The system of claim 1, wherein the algorithm is further configured to determine the one of the plurality of IMDs to be implanted in the patient in accordance with the battery performance parameters.

7. The system of claim 6, wherein the algorithm is configured to indicate the determined one of the IMDs to the user of the external device.

8. The system of claim 1, wherein the plurality of IMDs comprise at least one IMD having a rechargeable battery, and at least one IMD having a primary battery.

9. The system of claim 8, wherein the at least one battery performance parameter for the at least one IMD having a primary battery comprises information indicative of an estimated lifetime of the primary battery, and wherein the at least one battery performance parameter for the at least one IMD having a rechargeable battery comprises information indicative of an estimated recharging performance of the rechargeable battery.

10. The system of claim 9, wherein the estimated recharging performance comprises an estimated charging frequency and an estimated charging duration.

11. The system of claim 1, wherein the algorithm is further configured to determine from the stimulation program a current draw, and wherein the algorithm is configured to determine the at least one battery performance parameter for each of the plurality of IMDs at least in accordance with the current draw.

12. The system of claim 1, wherein the algorithm is further configured to determine from the stimulation program a current draw for each of the plurality of IMDs, and wherein the algorithm is configured to determine the at least one battery performance parameter for each of the plurality of IMDs at least in accordance with the current draw for each of the plurality of IMDs.

13. The system of claim 1, wherein the stimulation program comprises one or more electrodes of the IMD selected for stimulation, whether selected electrodes are anodes or cathodes, the magnitude of the stimulation, the frequency of the stimulation, and the duration of the stimulation.

14. The system of claim 1, wherein the external stimulator comprises an external trial stimulator configured to provide stimulation to the patient during a period preceding implantation of one of the plurality of battery-powered IMDs in the patient.

15. The system of claim 14, wherein the algorithm is further configured to determine the one of the plurality of IMDs to be implanted in the patient in accordance with the battery performance parameters.

16. A system, comprising:
    an external stimulator configured to provide stimulation to a patient in accordance with an IMD stimulation program; and
    an algorithm configured to be programmable in control circuitry of an external device to assess a first IMD having a rechargeable battery implantable in the patient and a second IMD having a primary battery implantable in the patient, wherein the algorithm is configured to determine at least one battery performance parameter for each of the first and second IMDs at least in accordance with the stimulation program.

17. The system of claim 16, wherein the at least one battery performance parameter for the second IMD comprises information indicative of an estimated lifetime of the primary battery, and wherein the at least one battery performance parameter for the first IMD comprises information indicative of an estimated recharging performance of the rechargeable battery.

18. The system of claim 17, wherein the estimated recharging performance comprises an estimated charging frequency and an estimated charging duration.

19. The system of claim 16, wherein the algorithm is further configured to determine one of the first IMD or second IMD to be implanted in the patient in accordance with the battery performance parameters.

20. The system of claim 16, wherein the algorithm is further configured to determine from the stimulation program a current draw, and wherein the algorithm is configured to determine at least one battery performance parameter for each of the first and second IMDs at least in accordance with the current draw.

21. The system of claim 16, wherein the algorithm is further configured to determine from the stimulation program a current draw for each of the first and second IMDs, and wherein the algorithm is configured to determine the at least one battery performance parameter for each of the first and second IMDs at least in accordance with the current draw for each.

* * * * *